(12) United States Patent
Rainin

(10) Patent No.: US 6,565,544 B1
(45) Date of Patent: May 20, 2003

(54) BLOOD REMOVAL DEVICE

(76) Inventor: Edgar A. Rainin, 111 Wild Oak Ct., Danville, CA (US) 94526

( * ) Notice: Subject to any disclaimer, the term of this patent is extended or adjusted under 35 U.S.C. 154(b) by 252 days.

(21) Appl. No.: 09/614,394

(22) Filed: Jul. 12, 2000

(51) Int. Cl.[7] ................................................ A61M 1/00
(52) U.S. Cl. ...................... 604/313; 604/289; 604/317
(58) Field of Search ........................... 604/1, 313, 315, 604/317, 289, 902

(56) References Cited

U.S. PATENT DOCUMENTS

| | | | |
|---|---|---|---|
| 3,969,498 A | | 7/1976 | Catania et al. |
| RE30,966 E | * | 6/1982 | Hargens et al. ............. 128/748 |
| 5,447,505 A | | 9/1995 | Valentine et al. |
| 5,466,231 A | | 11/1995 | Cercone et al. |
| 5,540,964 A | | 7/1996 | Mallen |
| 5,541,167 A | * | 7/1996 | Hsu et al. ...................... 514/56 |
| 5,599,330 A | | 2/1997 | Rainin |
| 5,628,735 A | * | 5/1997 | Skow ........................... 604/317 |
| 5,846,230 A | * | 12/1998 | Osborn, III et al. ......... 604/378 |
| 5,865,794 A | * | 2/1999 | Castro ............................ 604/53 |
| 5,928,174 A | | 7/1999 | Gibbins |
| 5,977,428 A | | 11/1999 | Bozigian et al. |

* cited by examiner

*Primary Examiner*—Weilun Lo
*Assistant Examiner*—Michael Bogart
(74) *Attorney, Agent, or Firm*—Theodore J. Bielen, Jr.

(57) ABSTRACT

A blood removal device utilizing a wicking element. The wicking element includes a surface exposed to blood and a zone within which is spaced from the exposed surface. An antithrombotic material is applied and held to the surface of the wicking element. A suction force is applied to the zone of the wicking element spaced from the surface exposed to the blood.

10 Claims, 2 Drawing Sheets

BLOOD REMOVAL DEVICE

BACKGROUND OF THE INVENTION

The present invention relates to a blood removal device particularly useful in medical procedures.

The removal of unwanted fluids during surgical procedures constantly poses a problem for surgeons and surgical assistants. For example, copious amounts of saline solutions are commonly used in eye surgery. Other surgical procedures, although not employing large quantities of irrigating solutions, generate blood from a bleeding source during such surgery.

Reference is made to U.S. Pat. No. 5,599,330 which represents a marked advance in the art of removing surgical irrigating solutions without trauma to surrounding tissues. However, although successful in removing blood atraumatically from a bleeding source during surgery for a short time, clotting of the blood within a few minutes clogs the wicking element found in devices described in U.S. Pat. No. 5,599,330. It is believed such clotting is due to the fine porous openings though the wicking element, which are sized in order to facilitate capillary action. However, such fine pore sizing exacerbates clogging due to clotting by blood and blood containing fluids.

It is known that clotting or coagulation is initiated by thrombin, formed from prothrombin, which facilitates the clotting of blood by catalyzing conversion of fibrinogen to fibrin. Antithrombotic or antithrombogenic materials are known, such as heparin. However, the application of most heparin compounds and/or complexes to wicking elements such as sponges with fine pores, although preventing the clotting of blood, also severely inhibits wicking. This is believed to be due to the naturally hydrophobic nature of such compounds or complexes.

Materials and combinations of materials have been proposed to transport or absorb moisture and blood from wounds. For example, U.S. Pat. No. 5,540,964 describes a moisture transport material which utilizes a hydrophilic synthetic material that is employed beneath a cast to reduce moisture conditions, promoting fungal and bacterial growth.

U.S. Pat. Nos. 5,447,505 and 5,977,428 show absorbent dressings for wounds which are intended to permit the removal of wound exudates, including blood, by the use of imbedded hydrogel particles and the predetermination of pore size with a particular polymeric material.

U.S. Pat. No. 5,928,174 shows a wound dressing device in which removal of moisture in the wound area is enhanced by forming absorbent material into a plurality of free floating strands.

U.S. Pat. No. 3,969,498 describes a wound dressing having a water-soluble body which may be aerated and foamed to adhere to wound tissue and form an artificial eschar or a scab.

U.S. Pat. No. 5,466,231 shows a laminated sponge device in which a polyvinyl acetate sponge body is laminated on multiple sides by a surface layer having perforations of a small pore size to permit fluids to pass through the laminate and be absorbed by the sponge body.

Relatively large diameter catheters have been coated with heparin in the past to prevent clotting or coagulation of blood while the catheters are used to deliver medications, blood components, fluids, hyperalimentation products, and to measure central venus pressure, in surgical situations.

Catheters have also been used in various cardiovascular procedures such as angioplasty and stent insertion. extract blood in surgical situations.

A blood removal device which employs wicking elements which are not clogged by the blood would be a notable advance in the medical field.

BRIEF SUMMARY OF THE INVENTION

In accordance with the present invention a novel and useful blood removal device is herein provided.

The system of the present invention includes a wicking element having a surface which may be exposed to blood and a zone within the wicking element which is spaced from the blood-contacting surface. The wicking element may take the form of polymeric materials formed into an open-cell configuration, a bundle of fine elongated fibers, a unitary body having a pore structure and the like. For example, low density polyethylene (LDPE), cellulose, polyvinyl acetyl, polyester, polyurethane and generally hydrophilic polymeric materials may be employed in this regard. The wicking element may be formed into a particular shape which is compatible with aspiration or suction devices. As is the case with the surgical wicking device disclosed in U.S. Pat. No. 5,599,330, the suction is normal and does not create a suction force on the surface of the wicking element in contact with the blood.

An antithrombotic material is applied to the surfaces of the wicking element to the extent that coagulation of blood is prevented and the wicking function of the wicking element is not inhibited. In certain cases heparin compounds and complexes may be employed in this regard. Of course other antithrombotic materials may be used. For example, heparin-benzalkoniium chloride (HBAC), 1.5% in isopropanol, heparin-tridodecylmethylammonium chloride (TDMAC), 2% in toluene, sodium or lithium heparin (NaHEP, LiHEP), 2% in deionized water serve as excellent sources of antithrombotic material which pervades the wicking element.

In many instances, the antithrombotic material is applied directly to the wicking element surfaces. In addition, a surfactant or surfactants may be used in conjunction with the antithrombotic material, HBAC, TDMAC, NaHEP, LiHEP and the like to insure wicking through the wicking element without affecting. the anticoagulation function provided by the antithrombotic material. In this regard, one or more surfactants may be employed in conjunction with a particular material used to construct the wicking element. Notably, silicone-glycol copolymer, ethoxylated esters, glycerin, and other hydrophilic surfactants have been found to be satisfactory in many cases in the present invention.

In addition, the surface of the wicking material may be modified using a plasma or corona treatment to provide a surface which readily accepts the antithrombotic, and in certain cases, surfactant material. It is believed that plasma or corona treatments provide an alteration of the surfaces of the wicking element and, in turn, allow better adherence of the antithrombotic material with or without a surfactant or surfactants. In the case of plasma treatment, nitrous oxide gas, oxygen gas, ammonia gas and the like have been proven to be satisfactory in the present invention.

It should be apparent that a novel and useful blood removal device has been herein above described.

It is therefore an object of the present invention to provide a blood removal device which uses a wicking element and an aspiration element which act in concert to remove blood from a surgical site without damaging tissue and at an acceptable rate.

Another object of the present invention is to provide a blood removal device which employs a wicking element that is capable of wicking blood for a relatively long period of time without clogging of the wicking element by coagulated blood.

Another object of the present invention is to provide a blood removal device which is useable in surgical operations in which blood must be removed from the surgical site from a bleeding source.

Another object of the present invention is to provide a blood removal device which is relatively easy to manufacture and employs proven biocompatible materials.

The invention possesses other objects and advantages especially as concerns particular characteristics and features which will become apparent as the specification continues.

For a better understanding of the invention reference is made to the following detailed description of the preferred embodiments which should be taken in conjunction with the hereinabove described drawings.

DETAILED DESCRIPTION OF THE PREFERRED EMBODIMENTS OF THE INVENTION

Various aspects of the present invention will evolve from the following detailed description of the preferred embodiments thereof which should be taken in conjunction with the hereinabove delineated drawings.

Figure 1:
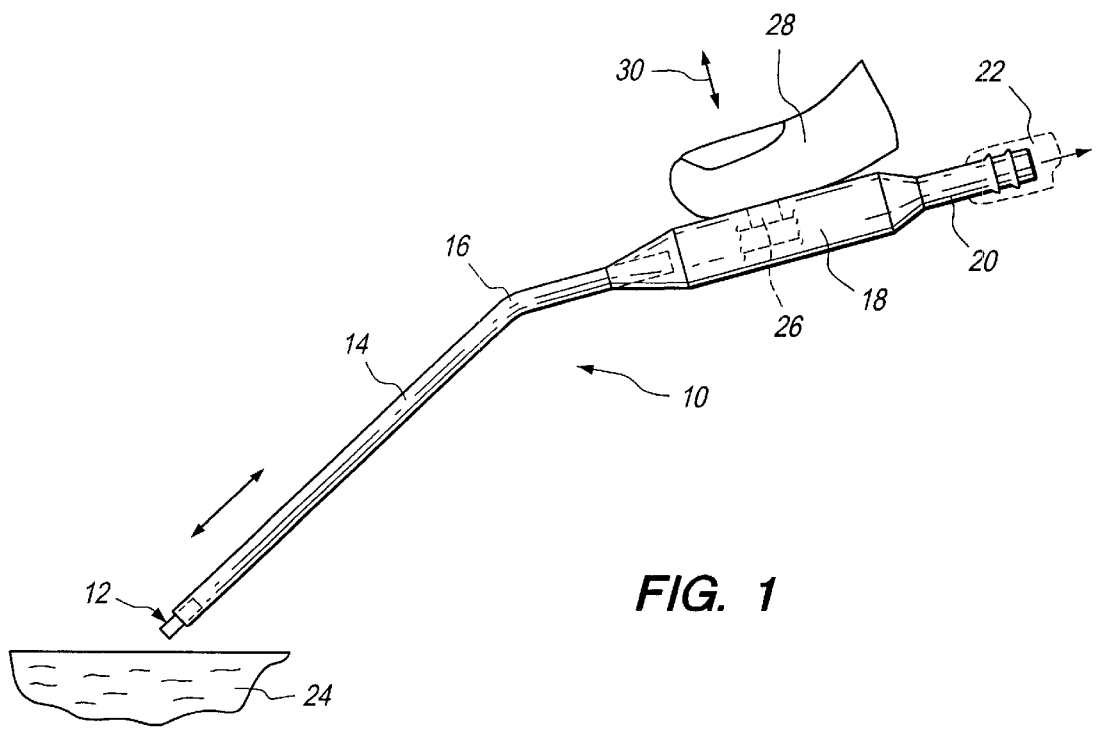
FIG. 1 is a side elevational view of the apparatus functioning as a blood removal device of the present invention.
Figure 2:
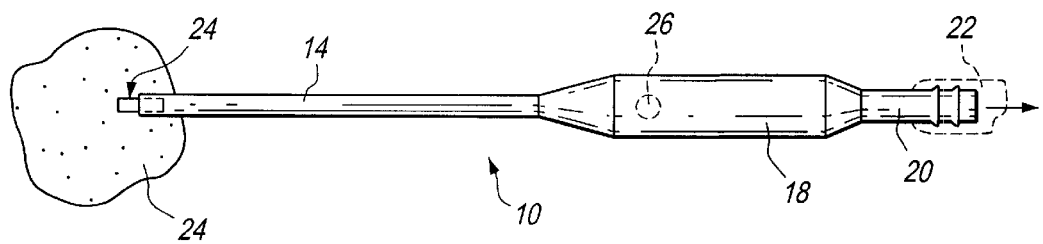
FIG. 2 is a top plan view of the apparatus depicted in FIG. 1.

The invention as a whole is depicted in the drawings by reference character 10. Blood removal device 10 includes as one of its main aspects, a wicking element 12. Wicking element 12 may be formed into a cylinder formed to fit within hollow tube 14. Tube 14 includes an angulated portion 16 and terminates in a hollow handle 18. Suction or aspiration is applied to the end 20 of hollow handle 18 to a fitting 22, shown in phantom, by a suction source (not shown) of conventional configuration. Device 10 is placed into blood body 24. Optionally, hollow handle 18 may include a vent opening 26 which can be partially or completely closed by thumb 28. Such optional configuration, directional arrow 30, shows the movement of thumb 28 to regulate the suction pressure within tube 14. It should be noted that other valve means may be employed to achieve such suction control. However, it has been found that such suction pressure within tube 14 may be controlled by an aspiration pump or suction source (not shown) of conventional configuration connected to fitting 22 which fits on handle 18, FIGS. 1 and 2.

Wicking element 12 may be formed of generally porous material such as a porous sponge material, bundled fibers, or any other material providing fine pores for the wicking of liquids by capillary action. In this regard, wicking element may be composed of polyolefinic material such as polyethylene, polypropylene, and other polymeric structures such as polyvinyl acetyl. An average red blood cell measures 7 to 8 microns in diameter while the average white cell in blood measures 14 to 15 microns. Blood platelets are much smaller in diameter than the red or white cells. Wicking member 12 should have a pore size greater than the size of the components of blood. For example, a 50-micron pore size would be satisfactory in this regard. It has been found that low-density polyethylene fibers manufactured under the designation Transorb R-21001 and R-20942, by American Filtrona Corp. of Richmond, Va., are suitable. In addition, polyvinyl acetyl manufactured by Hydrofera of Willimantic, Conn., have proved particularly useful as wicking element 12. It should be noted that the polyethylene wicking element 12 is formed into a bundle of fibers, while the polyvinyl acetyl wicking element is formed into a sponge material.

Figure 3:
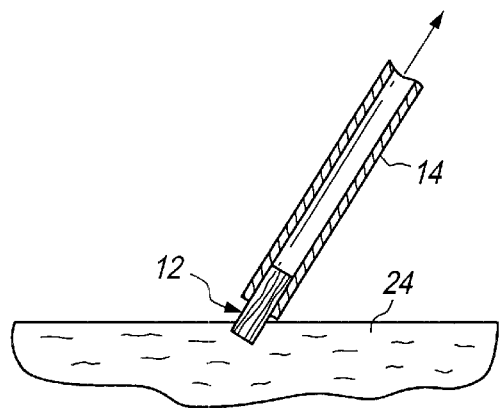
FIG. 3 is a sectional view of the tip portion of the device of FIGS. 1 and 2 showing the wicking element in contact with a body of blood.
Figure 4:
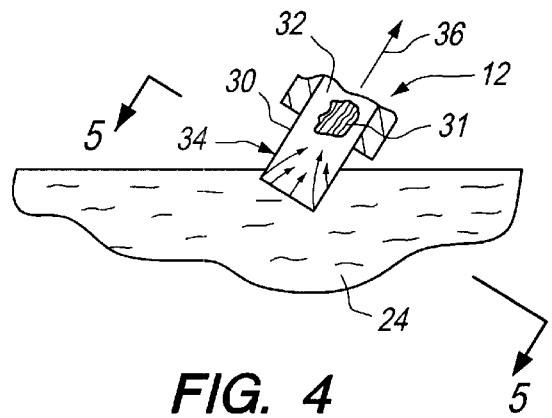
FIG. 4 is an enlarged sectional view of the wicking element depicted in FIG. 3.
Figure 5:
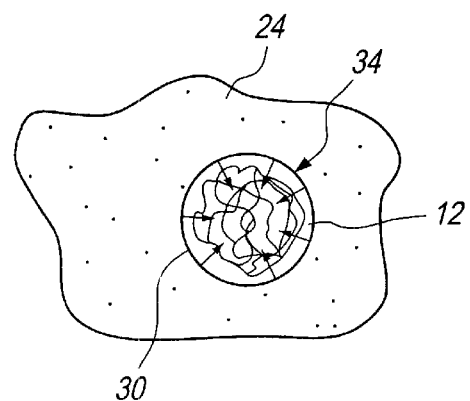
FIG. 5 is a sectional view taken along FIG. 5—5 of FIG. 4.

Wicking element 12 is treated with an antithrombotic material. With respect to FIGS. 3, 4, and 5, wicking element 12 includes an outer surface 30 and an inner zone 32 within wicking element 12 that is spaced from outer surface 30. An antithrombotic material is applied to wicking element 12 and held at outer surface 30, as well as other inner surfaces 31 at inner zone 32 within wicking element 12. Although many antithrombotic materials tend to be hydrophobic, it has been found that application of the same to wicking element 12 maintains the wicking ability of wicking element 12 (capillarity), and also prevents coagulation of blood, deriving from blood body 24, while passing through wicking element 12. FIG. 4 depicts the wicking of blood 24 from outer surface 30 to inner zone 32 of wicking element 12 by plurality of arrows 34. Once drawn into inner zone 32 of wicking element 12, blood 24 is aspirated within zone 32, only, by a suction force, depicted by arrow 36. In most surgical procedures, antithrombotic activity in wicking element 12 must take place over a relatively short period of time, typically measured in hours. In this respect, heparin-benzalkonium chloride (HBAC), 1.5% in isopropanol, heparin-tridodecylmethylammonium chloride (TDMAC), 2% in toluene, or sodium heparin (NaHEP), 2% in deionized water have proven satisfactory as the antithrombotic material applied to wicking element 12.

Also, one or more surfactants may be applied to surfaces 30 and 31 of wicking element 12 to enhance the wicking ability of wicking element 12 when an antithrombotic material has also been applied and held to wicking element 12. For example, silicone, silicone glycol polymer, ethoxylated esters, glycerin, and other materials have been found to be satisfactory in this regard.

Moreover, outer surface 30 of wicking element 12 may be prepared prior to the application of antithrombotic material and/or surfactant (S). For example, plasma treatment using oxygen gas or nitrous oxide gas has been deemed to aid in the application of the antithrombotic and surfactant materials to wicking element 12.

The following Examples are intended to illustrate specific applications of the invention, but are not deemed to limit the invention in any manner.

EXAMPLE I

A device described in U.S. Pat. No. 5,599,330 was employed to remove blood during eyelid surgery to avoid trauma deriving from aspiration techniques used in the prior art. The wicking member of the device was constructed of a polyvinyl acetyl (PVA) constructed in a sponge-like material having fine pores. The sponge like material is generally described as an open-cell type material. Although the blood was wicked away from the surgical site for a period of about 2 minutes, the device ceased to operate when the blood began to clot.

EXAMPLE II

Surgical wicking devices of the type described in U.S. Pat. No. 5,599,330 were manufactured each using a standard 12 French Frazier hand piece manufactured by Con Med Corporation of Utica, N.Y. A wicking member was bonded to the tip of the cannula of each hand piece using a 10 mm long Transorb wick R-16398 from American Filtrona Corp. of Richmond, Va. The wicking member was bonded to the cannula using medical grade cyanacrylic adhesive. 5 mm of the wicking member protruded from the cannula end when adhesion was completed. All hand pieces were sterilized using ethylene oxide gas. Each of the wicking elements in the hand pieces were coated with a surfactant. Several of the hand pieces were employed to wick away blood during a Rhytidectomy operation. The wicking of blood went exceedingly well for approximately 2 to 4 minutes until the blood began the clot. After this time wicking ceased. The wicking elements were rinsed in sterile saline which permitted wicking for a short period of time until further clotting took place.

EXAMPLE III

The hand pieces of Examples I and II were again constructed using wicking elements manufactured of a bonded polyolefin fiber sold under the name Transorb R-20945 manufactured by Filtrona Richmond of Richmond, Va. The Transorb wicks included a "standard surfactant finish". The wicks were coated secondarily with STS Biopolymer standard 1.5 percent heparin benzalkonium chloride (HBAK) in isopropyl alcohol. The wicking elements were tested for the prevention of coagulation of blood by contacting the same with fresh rabbit blood. It was discovered that there was profound anticoagulation activity lasting over 24 hours. The wicking elements were then tested for wicking and it was found that wicking occurred at an excellent rate.

EXAMPLE IV

A polyvinyl acetyl 8 mm×3.18 mm diameter sponge was coated with 1.5% HBAC and silicone-glycol co-polymer with the designation DC193-IPA manufactured by Dow Corning. The wicking time from a blood source along the length of the wicking element was measured at approximately 2 seconds. Without use of the surfactant, the wicking time was measured at approximately 2 to 3 seconds. Blood was observed not to coagulate for a time period extending beyond 1 hour.

EXAMPLE V

Wicking elements manufactured from fiber bundles were obtained from American Filtrona Corp. of Richmond, Va. under the designation Transorb. A wick designated R-20942 8 mm×3.18 mm diameter, having a fiber density of 0.148 g/cc and coated with 1% ethoxylated esters was further coated with HBAC and a silicone surfactant manufactured by Dow Corning. The wick was dried at 50 degrees centigrade for 45 minutes. Wicking of blood was then tested and it was determined to take place within 1 second, in the dry and moist modes.

A R-21001 8 mm×3.18 mm diameter wicking element having a fiber density of 0.135 g/cc was employed and coated with HBAC 1.5% and a silicone-glycol surfactant manufactured by Dow Corning. The wicks were dried at 50 degrees centigrade for 45 minutes. Wicking time of blood was measured at 1 second in the dry or moist modes.

Further R-21001 wicks were treated with nitrous oxide or oxygen gas plasma for several minutes. After a time period, ranging from 18 hours to 15 days, the wicks were coated with HBAC and the silicone-glycol surfactant manufactured by Dow Corning. All the wicks were allowed to dry at 50 degrees centigrade for 45 minutes. Wicking time was measured between 1 and 2 seconds in the dry mode. In the moist mode, the wicking time increased to 1 second or a fraction above 1 second. Coagulation of blood did not occur in each wicking element for several hours.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A blood removal device utilizing a suction source, comprising:

a a wicking element, said wicking element including an outer surface exposed to blood and a zone within said wicking element spaced from said outer surface, said zone including inner surfaces;

b an antithrombotic material applied and held to said outer and inner surfaces of said wicking element; and c means for applying a suction force only to said inner zone of said wicking element spaced from said outer surface exposed to the blood, said means for applying a suction force including a tube having a bore, said wicking element extending into a portion of said bore and leaving the remaining portion of said bore unencumbered, said wicking element projecting a certain distance from said tube.

2. The blood removal device of claim 1 in which said wicking element comprises a stranded material.

3. The blood removal device of claim 1 in which said wicking element is constructed of material selected from the group essentially comprises:

polyvinyl acetyl, polyethylene, and polypropylene.

4. The blood removal device of claim 1 which additionally comprises at least one surfactant applied to said wicking outer and inner surfaces.

5. The blood removal device of claim 1 which additionally comprises at least one surfactant applied to said antithrombotic material at said outer and inner surfaces of said wicking element.

6. The blood removal device of claim 4 in which said at least one surfactant comprises a pair of surfactants.

7. The blood removal device of claim 5 in which said at least one surfactant comprises a pair of surfactants.

8. The blood removal device of claim 5 in which said at least one surfactant is selected from the group essentially comprising:

silicone, silicone-glycol polymer, ethoxylated ester, and glycerin.

9. The blood removal device of claim 1 in which said antithrombotic material is selected from the group comprising essentially:

heparin-benzalkonium chloride, heparin-tridodecyl-methylammonium chloride, and sodium heparin.

10. The blood removal device of claim 1 in which said wicking element comprises an open cell material.

* * * * *